United States Patent
Hashim et al.

(10) Patent No.: US 8,907,070 B2
(45) Date of Patent: Dec. 9, 2014

(54) GLYCOLIPIDS OF BRANCHED CHAIN ALKYL OLIGOSACCHARIDES FOR LIQUID CRYSTAL AND RELATED APPLICATIONS

(71) Applicants: Rauzah Hashim, Kuala Lumpur (MY); Thorsten Heidelberg, Kaula Lumpur (MY); Hind Hassan, Kuala Lumpur (MY); Nasrul Zamani Mohd Rodzi, Kuala Lumpur (MY); Rusnah Syahila Dauli Hussen, Kualu Lumpur (MY); Ahmad Sazali Hamzah, Selangor (MY); Shahidan Radiman, Selangor (MY); Volkmar Vill, Hamburg (DE); Matthias Wulf, Hamburg (DE); Seiji Ujiie, Shimane (JP)

(72) Inventors: Rauzah Hashim, Kuala Lumpur (MY); Thorsten Heidelberg, Kaula Lumpur (MY); Hind Hassan, Kuala Lumpur (MY); Nasrul Zamani Mohd Rodzi, Kuala Lumpur (MY); Rusnah Syahila Dauli Hussen, Kualu Lumpur (MY); Ahmad Sazali Hamzah, Selangor (MY); Shahidan Radiman, Selangor (MY); Volkmar Vill, Hamburg (DE); Matthias Wulf, Hamburg (DE); Seiji Ujiie, Shimane (JP)

(73) Assignee: Universiti Malaya, Kuala Lumpur (MY)

( * ) Notice: Subject to any disclaimer, the term of this patent is extended or adjusted under 35 U.S.C. 154(b) by 0 days.

(21) Appl. No.: 13/668,632

(22) Filed: Nov. 5, 2012

(65) Prior Publication Data
US 2013/0150567 A1 Jun. 13, 2013

Related U.S. Application Data

(62) Division of application No. 11/908,791, filed as application No. PCT/SG2006/000033 on Feb. 20, 2006, now Pat. No. 8,304,525.

(30) Foreign Application Priority Data

Mar. 15, 2005 (MY) .................. PI20051074

(51) Int. Cl.
C07H 15/04 (2006.01)
C07H 15/08 (2006.01)
C09K 19/04 (2006.01)

(52) U.S. Cl.
CPC ............ *C07H 15/04* (2013.01); *C09K 19/0422* (2013.01)
USPC .......................... 536/4.1; 536/17.2; 536/18.3

(58) Field of Classification Search
None
See application file for complete search history.

(56) References Cited

PUBLICATIONS

Yoshikawa et al. Phytochemistry, vol. 34, Issue 5, Nov. 1993, pp. 1431-1433, abstract only.*
Yasuda et al. JP 09-020628, Jan. 21, 1997, machine translation.*
von Minden et al. Journal of Colloid and Interface Science 236, 108-115 (2001).*
Hashim et al. Electronic-Liquid Crystal Communications, Feb. 20, 2003, pp. 1-17.*
Milkereit et al. Chemistry and Physics of Lipids 127 (2004) 47-63.*
Hashim et al. Thin Solid Films 509 (2006) 27-35.*

* cited by examiner

*Primary Examiner* — Layla Bland
(74) *Attorney, Agent, or Firm* — Preston Smirman; Smirman IP Law, PLLC

(57) ABSTRACT

Glycolipids of branched chain alkyl oligosaccharides include a primary alcohol branched in the 2-position and an oligosaccharide, covalently bond to the alcohol in either α- or β-linkage (shown in Formula I and Formula II). These compounds show phase behavior not found for the corresponding straight chain counterparts. The properties involve an ambient temperature liquid crystalline appearance and thermotropic liquid crystal phase polymorphism. The formation of cubic phases is considered most interesting with respect to life science applications, e.g. liposomes for drug delivery. Depending on the choice of sugar head group and alkyl tail, various levels of water miscibility may be adjusted to meet applications requirements (complete solubility for emulsifier applications, e.g. cosmetic creams, to limited water swelling only, e.g. for the preparation of artificial membranes). The closed structural relationship to natural lipids also makes branched chain alkyl oligosaccharides valuable subjects for biochemical investigations, e.g. membrane studies.

2 Claims, 4 Drawing Sheets

Formula I: Branched chain alkyl oligosaccharide, (1,4)-linked

Formula II: Branched chain alkyl oligosaccharide, (1,6)-linked

Core-structure (monosaccharide) of a natural glycoglycerolipid

Synthesis of branched chain alkyl maltosides (analog syntheses for other oligosaccharides)

Derivatization of alkyl 1,4-linked disaccharides
(analog reactions for other oligosaccharides)

DSC spectrum for a branched chain maltoside

GLYCOLIPIDS OF BRANCHED CHAIN ALKYL OLIGOSACCHARIDES FOR LIQUID CRYSTAL AND RELATED APPLICATIONS

CROSS-REFERENCE TO RELATED APPLICATION

This application is a division of, and claims priority to, U.S. patent application Ser. No. 11/908,791 filed Apr. 17, 2008, now U.S. Pat. No. 8,304,525, issued Nov. 6, 2012, which is a national phase of PCT International Patent Application Serial No. PCT/SG2006/000033, filed Feb. 20, 2006, which claims priority to Malaysian Patent Application Serial No. PI 20051074, filed Mar. 15, 2005, the entire specifications of all of which are expressly incorporated herein by reference.

FIELD OF THE INVENTION

The present invention relates to glycolipids, more particularly, it relates to glycolipids comprising an alcohol branched in the 2-position that is covalently bonded to an oligosaccharide in either α- or β-linkage. The present invention also relates to liquid crystalline properties and self assembly of these glycolipids, which give rise to applications of these materials for surfactants, artificial membranes and medicines.

BACKGROUND OF THE INVENTION

Alkyl glycosides are compounds comprising a carbohydrate and an alcohol, chemically bound in a cyclic acetal. Compounds involving alkyl groups exceeding $C_5$ belong to a class of compounds called glycolipids, which are commonly known to show surfactant properties and have acquired some industrial impact for special application fields. Their role in biology is widely acknowledged.

Most of the applications for synthetic glycolipids rest on their molecular properties as described in U.S. Pat. Nos. 3,219,656, 3,547,828, 3,839,318 and EP 041960. These properties fall into two broad categories: adsorption and self assembly. The first indicates interfacial properties on water/oil, water/air or solid/gas interfaces. Connected applications are focusing on wetting, foaming, detergency and emulsions. The most important industrial roles of surfactants are connected with the formation of emulsions and with detergency. An emulsion is a dispersion of two normally immiscible fluids; thus emulsions are multiphase systems even though they might appear to look homologue. Detergency is responsible for most cleaning purposes. Both rheology (flow properties) and kinetics of mesophase formation (any non crystalline kind of self assembly of matter) in surfactant systems has high potential impact on manufacturing processes, since rheology might limit the handling of processes. Self assembly is the ability of matter to form supramolecular structures. Examples cover micelles, bilayers and other liquid crystals which all may exhibit applications on their own.

The liquid crystalline behavior of alkyl glycosides has been subject to several investigations (e.g. D. E. Koeltzow et al., *J. Am. Oil Chem. Soc.*, 1984, 61, 1651; V. Vill et al., *Liq. Cryst.*, 1989, 6, 349-356). However, while carbohydrate derived compounds have been found useful as additives for liquid crystal based switches with respect to their high optical twisting power (V. Vill et al., *Z. Naturforschung A*, 1989, 44, 675-679), alkyl glycosides so far did not acquire usage for liquid crystal applications. Their liquid crystal phase temperature range resemble a major disadvantage. Pure compounds exhibit liquid crystallinity only at temperatures higher than ambient temperature. Most technical applications, however, require (or at least favor) lower temperatures. The present invention enables the formation of liquid crystal phases for alkyl glycosides at room temperature.

The use of alkyl glycosides for surfactant purposes has been described in several patents and papers (e.g. U.S. Pat. No. 9,908,517, WO 0190286). Suitable applications cover the use as detergent for cleaning purposes (e.g. U.S. Pat. No. 5,858,954, MY 106677) as well as additives for e.g. cosmetic formulations (e.g. WO 9406408, U.S. Pat. No. 5,605,651, JP 9173822). A related example for usage in vesicles may be found in German Patent DE 1963437. Commonly alkyl glycosides (also named APGs, or alkyl polyglycosides) contain only one single alkyl chain. This way they differ from natural lipids, which exhibit a double chain structure, involving a polar head-group and two non-polar chains. These structures, showing special physical characteristics generally believed to be responsible for the properties of biological membranes, cannot be mimicked by simple APGs.

For biophysical studies, therefore, more complex compounds, like glycoglycerolipids, are needed. Due to immense problems involved in lipid purification, generally synthetic compounds are favored over natural derived material. The number of chemical transformations involved and the extensive purification, however, make this approach expensive and limits future applications. A major obstacle is based on the limited chemical stability of the ester groups present in glycoglycerolipids. These add to both purification requirements and the number of chemical steps. While syntheses for ether analog structures have been published (e.g. H. Minamikawa et al., *Chem. Phys. Lipids*, 1994, 72, 111-118), improving the accessibility of materials, a more easy access to model compounds remains desirable. The present invention provides such a possibility.

Branched chain (guebert type) alcohol derived esters have been applied as emulsifiers before, showing superior emulsification and better liquidity (e.g. U.S. Pat. No. 5,717,119, 5,736,571, 6,013,813). The effect of branching on alcohols bond in glycosides, however, has not been investigated before.

Synthetic glycolipids exhibit a large spectrum of useful applications such as coating a drug to keep it from early destruction, stabilization of hydrocarbon foam, primary solvents for tropical medication, mild soap for delicate fields of application or the synthesis of nanostructure materials. Prior art Japanese Patent JP 11244608 even disclosed the usage of glycolipid derivatives as antifoaming additives for resin manufacturing, dyeing and wastewater treatment.

The objective of the invention is to provide new glycolipids showing special liquid crystal properties with respect to thermotropic and lyotropic behavior. Possible applications of these glycolipids involve:
 low temperature liquid crystals, e.g. for optical switches and other applications
 artificial membranes
 drug coating and related pharmaceutical applications (e.g. vesicles)
 surfactant and micelle applications in cosmetics, detergency and nanotechnology
 antifoaming surfactants for process- and wastewater treatments

SUMMARY OF THE INVENTION

The inventors have investigated the liquid crystalline properties of branched chain alkyl oligosaccharides with the intention of providing novel easy accessible synthetic glycolipids suitable for model studies on membranes.

During this investigation it turned out, that the synthetic glycolipids show particular interesting liquid crystalline properties with respect to both thermotropic and lyotropic behavior, not being found for previously know straight chain alkyl saccharides. Features involve ambient temperature liquid crystalline appearance and thermotropic polymorphism, including observation of cubic phases. The latter are considered particularly interesting with respect to life science applications like e.g. liposomes for drug delivery.

Beside their unusual thermotropic liquid crystalline behavior, glycolipids of branched chain oligosaccharides also exhibit mesophases in aqueous environment, demonstrating their surfactant abilities. The close structural relationship towards natural glycoglycerolipids combined with their increased chemical resistance make them interesting subjects for pharmaceutical applications.

Based on accessibility and costs, the focus is set on nature derived reducing oligosaccharides. These especially involve but do not limit to malto-, cello-, chito- and xyloologomers as well as lactose, isomatose, gentio- and meliobiose.

The glycolipids of the present invention may be summarized in Formula I, where
A=H, $CH_2Y$, $CH_3$, $CO_2R^*$, $CO_2M$, $COSR^*$, $CSOR^*$, $CONR^*R^{**}$, $C_2H_4X$, $CH_2CO_2R^*$, $CH_2COSR^*$, or $CH_2CONR^*R^{**}$;
L=H, sugar or acetylated sugar;
M=cation;
$R^3$=H, Ac, or $H(C_2H_4O)_x$ or $W(C_2H_4O)_x$;
$R^{3'}$=H, Ac, or $H(C_2H_4O)_x$ or $W(C_2H_4O)_x$;
W=OH, $NH_2$, NHC(=W *)$R^*$, NHC(=W *)$Y^*R^*$, or $O(C_2H_4O)_xR^*$;
Y=W, Cl, Br, F, $N_3$, or CN;
$R^*$, $R^{**}$=(substituted)alkyl, aryl, or H;
W *, Y*=O, S, or $NR^{**}$;
X is an integer of 1 to 100;
n, m≥2 and m≠n;
d, d'=1, −1.

In another embodiment of the present invention, glycolipids of branched chain alkyl oligosaccharides show structures according to Formula II, where
A=$CH_2Y$ $CH_2OL$, $CH_3$,$CO_2R^*$, $CO_2M$, $COSR^*$, $CSOR^*$, $CONR^*R^{**}$, $C_2H_4W$, $CH_2CO_2R^*$, $CH_2COSR^*$, or $CH_2CONR^*R^{**}$;
L=sugar, or acetylated sugar;
M=cation;
$R^2$=H, Ac, or $H(C_2H_4O)_x$ or $W(C_2H_4O)_x$;
$R^{2'}$=H, Ac, or $H(C_2H_4O)_x$ or $W(C_2H_4O)_x$;
$R^3$=H, Ac, or $H(C_2H_4O)_x$ or $W(C_2H_4O)_x$;
$R^{3'}$=H, Ac, or $H(C_2H_4O)_x$ or $W(C_2H_4O)_x$;
$R^4$=H, Ac, or $H(C_2H_4O)_x$ or $W(C_2H_4O)_x$;
$R^{4'}$=H, Ac, or $H(C_2H_4O)_x$ or $W(C_2H_4O)_x$;
W=OH, $NH_2$, NHC(=W *)$R^*$, NHC(=W *)$Y^*R^*$, or $O(C_2H_4O)_xR^*$;
Y=W, Cl, Br, F, $N_3$, or CN;
$R^*$, $R^{**}$=(substituted) alkyl, aryl, or H;
W *, Y*=O, S, or $NR^{**}$;
X is an integer of 1 to 100;
n, m≥2 and m≠n;
d d'=1,−1.

The further subject of the present investigation is focused on the use of the glycolipids described before and their patterns of self assembly for pharmaceutical, cosmetic or other applications, especially with respect to the life science sector.

DETAILED DESCRIPTION OF THE INVENTION

Several branched chain alkyl oligosaccharides show ambient temperature liquid crystalline behavior. While common alkyl glycosides generally exhibit exclusively smectic phases, more complex phase diagrams can be observed for branched alkyl glycosides. Thus smectic, columnar and even liquid crystal phase polymorphism involving bicontinuous cubic phases may be found. The liquid crystal-liquid crystal phase transitions may give rise to some new applications of the compounds.

Figure 3:
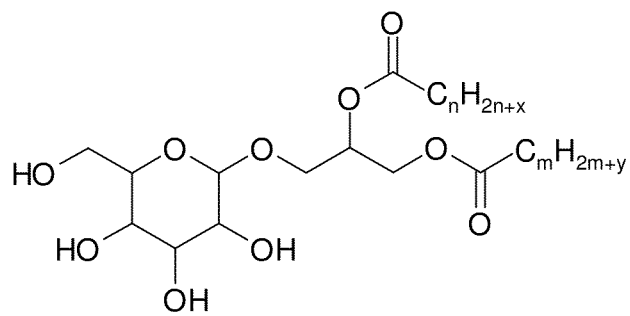
FIG. 3 shows the core structure of a natural glycoglycerolipid.

Branched alkyl glycosides are almost isosteric to natural glycoglycerolipids (see FIG. 3). Thus the branched alkyl oligosaccharides provide interesting candidates for new biotechnology applications as well as pharmaceutical applications. Based on their complex phase behavior, they may also exhibit superior properties for cosmetic formulations as e.g. creams.

Figure 1:
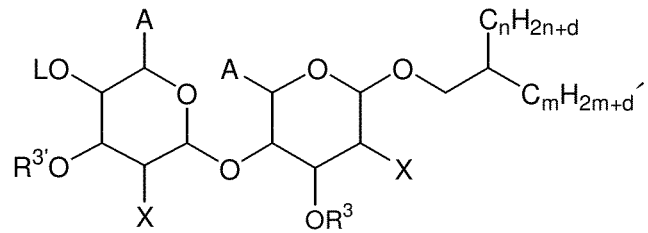
FIG. 1 shows the branched chain glycolipid containing a (1,4)-linked saccharide.
Figure 2:
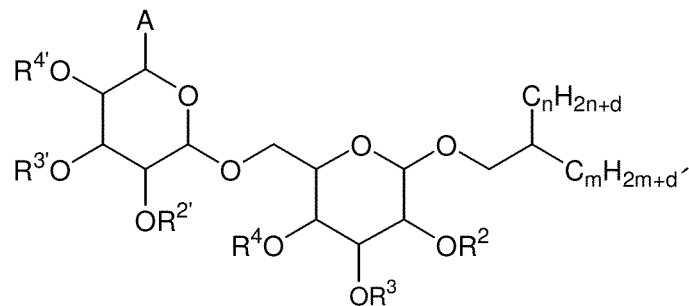
FIG. 2 shows the branched chain glycolipid containing a (1,6)-linked saccharide.
Figure 4:
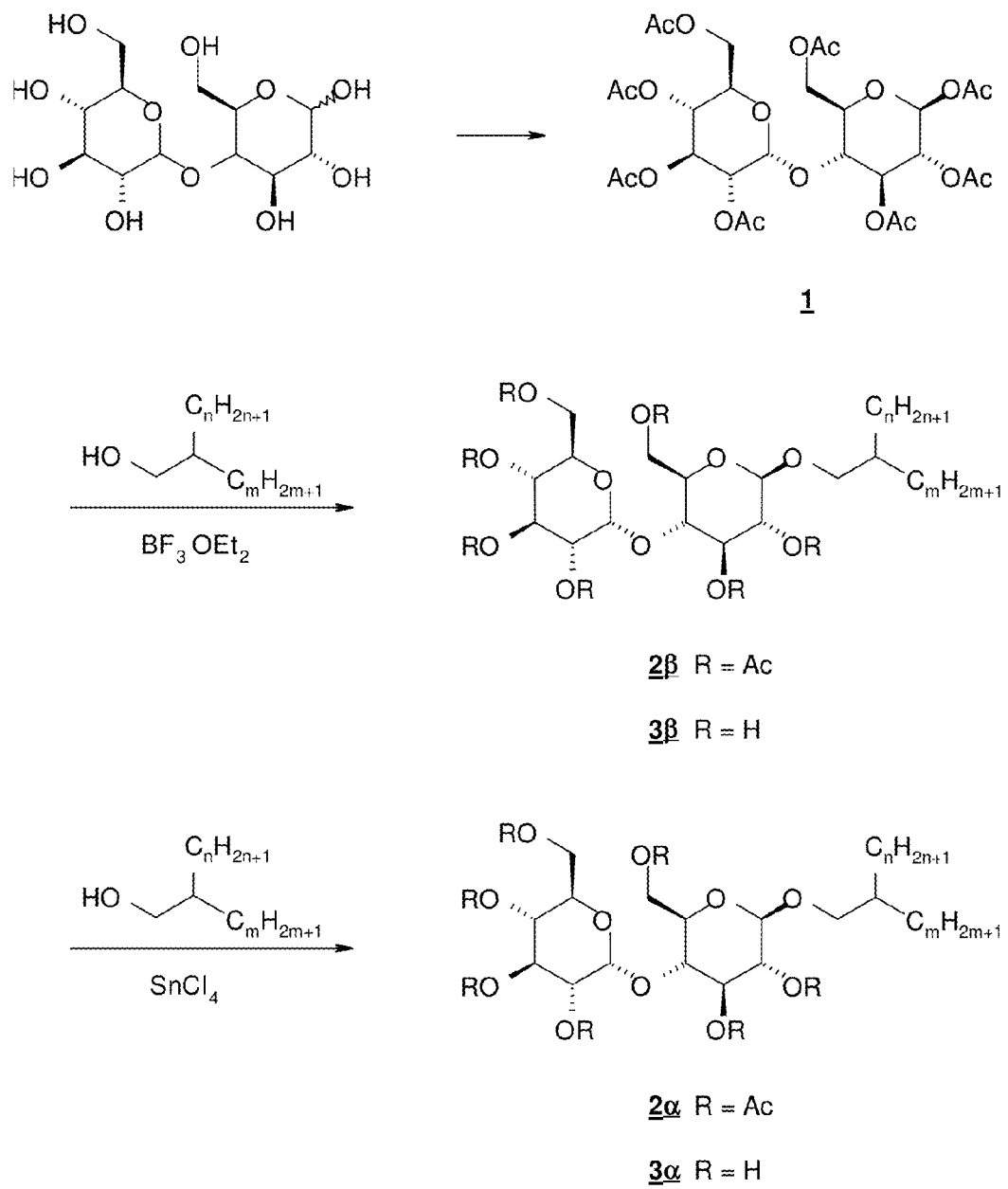
FIG. 4 shows the synthesis route for branched chain alkyl α- and β-oligosaccharides, exemplified for a maltosides.
Figure 5:
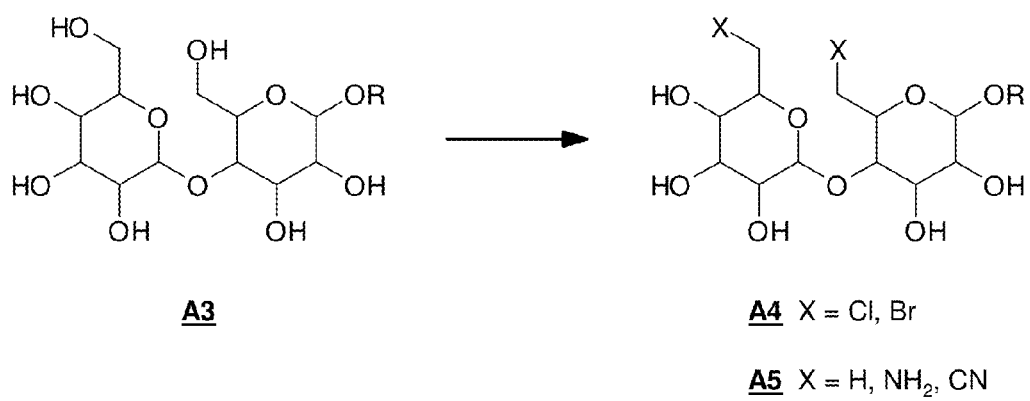
FIG. 5 shows the derivatization of branched chain glycolipids, of (1,4)-linked disaccharides.
Figure 5:
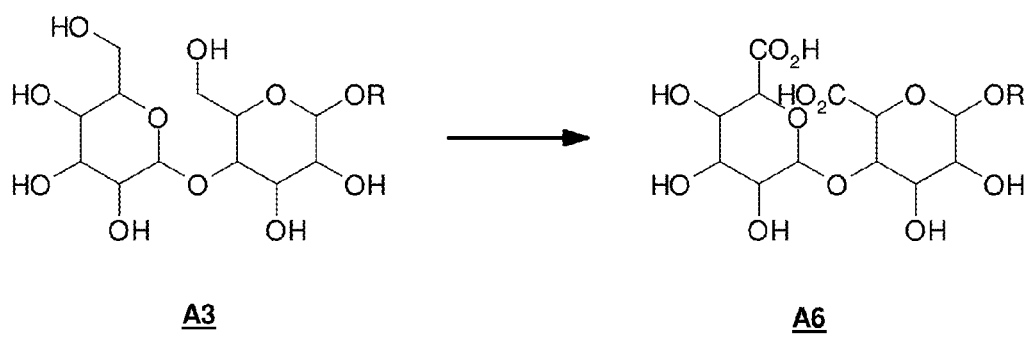
Figure 6:
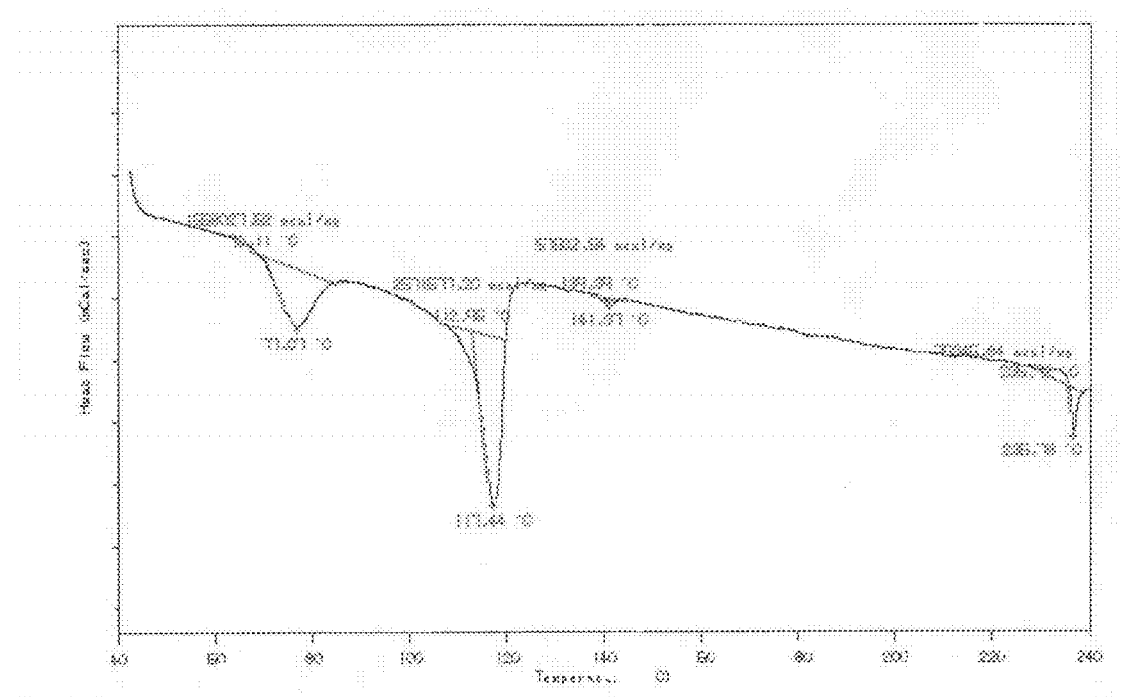
FIG. 6 shows a DSC recording for a branched chain alkyl maltoside.

The preparation of the compounds comprises a 3-step-synthesis starting from commercial available nature derived oligosaccharides following literature known procedures (e.g. V. Vill et al., *Liq. Cryst.*, 1989, 6, 349-356; FIG. 4). Derivatization (FIG. 5) of these products provide access to an even greater variety, which may be further improved taking advantage of amino or carboxyl-groups. The full range of structures available through this process is displayed in FIG. 2.

The thermotropic phase behavior of branched chain alkyl oligosaccharides involve a change of liquid crystal phases found for a specific sugar head group from singly smectic, over liquid crystal polymorphism, towards a singly columnar liquid crystal mesophase with increasing size of alkyl chain. Most interesting among this is the appearance of bicontinous cubic phases separating the smectic and the columnar structures. Cubic phases are believed to play an essential role in cell-exchange processes. All processes involving endo- and exocytosis pass through a cubic state of the membrane. Cubic phases of membrane like material, therefore, are considered interesting with respect to possible life science applications. Cubic phases for branched chain alkyl oligosaccharides may be observed over a broad range of temperature. Experiments also indicate the presence of two different cubic phases for at least one of the compounds.

The lyotropic liquid crystal behavior in aqueous systems conforms the compounds' ability to act as structure forming surfactants. The thermal stability of the supramolecular structures formed depends on the length of the alkyl chain of the glycolipid. For some compounds textures be maintained over a broad temperature range, starting below room temperature and exceeding 80° C. The water miscibility of branched chain alkyl oligosaccharides for a given sugar head varies largely, depending highly on the length of the alkyl tails. Based on the applications requirements, either full water solubility (e.g. for emulsion applications) or mere slight, water swelling of the glycolipids (e.g. for the formation of artificial membranes, since rearrangement of the material or even dissolving is to be avoided in that case) may be achieved.

In another embodiment, glycolipids of branched chain alkyl oligosaccharides of the present invention, or mixtures containing one or more of them, may be used in thermotropic liquid crystal applications, cosmetical applications, vesicles or liposomes preparation, especially for drug delivery, pharmaceutical emulsions, pharmaceutical applications, where the role of the compound is either protection, time release or direction of a drug or diagnostic sensor, lyotropic liquid crystal applications, especially for the preparation of artificial membranes, nanostructure templating, as antifoaming additives for process- or wastewater treatments, surfactant or any other suitable applications known in the art. The use of glycolipids for drug delivery system in the present invention aims to enhance permeability of the drug delivery system into the cells across the cell membrane rather than contributing as a specific antigen, which is used for targeting in receptor recognitions found in common drug delivery system.

The following examples are included herein solely as an illustrative aid to provide a more cotnnlete understanding of the present invention and the product formed thereby. The examples do not limit the scope of the present invention disclosed and claimed herein in any fashion.

EXAMPLES

General Synthesis of β-Glycosides (Amounts Based On Branched $C_{24}$ Disaccharide Glycosides)

A solution of 3.4 g β-peracetate and 2.3 g 2-decyl-tetradecanol in 50 mL anhydrous dichloromethane was treated with 600 μL borontrifluoride dimethyletherate and kept at room temperature for about 5-48 h. The mixture was washed with aqueous sodium bicarbonate and dried over magnesium sulfate. After evaporation of the solvent, the acetylated glycolipid was purified by chromatography (hexane/ethyl acetate). The intermediate product was dissolved in 30-40 mL methanol and treated with a catalytic amount of sodium methoxide. After 30-60 min the catalyst was removed by treatment with amberlite IR 120 ($H^+$) and the solvent was evaporated. Further purification of the anomer by chromatography on ion exchanging resin generally proofed to be unnecessary.

General Synthesis of α-Glycosides (Amounts Based on Branched $C_{24}$ Disaccharide Glycosides)

A solution of 3.4 g β-peracetate and 2.7 g 2-decyl-tetradecanol in 50 mL anhydrous dichloromethane was treated with 600 μL tin tetrachloride and kept at room temperature for about 2-3 d. The reaction mixture was filtered through moistened celite, then washed with aqueous sodium bicarbonate and dried over magnesium sulfate. After evaporation of the solvent, the acetylated glycolipid was purified by chromatography (hexane/ethyl acetate). The intermediate product was dissolved in 30-100 mL methanol and treated with a catalytic amount of sodium methoxide. After ½-3 h the catalyst was removed by treatment with amberlite JR 120 ($H^+$) and the solvent was evaporated. Further purification of the anomer by chromatography on ion exchanging resin was generally not required.

Example 1

2-Hexyl-decyl-α-meliobioside

Yield: 28%; Cr? SmA 170° C. Dec $^1$H-NMR (300 MHz, $CDCl_3$, peracetate): δ 5.45 (dd, H-3; 10.0 Hz, 9.5 Hz), 5.44 (dd, H-4'; 3.0 Hz, 1.0 Hz), 5.31 (dd, H-3'; 10.5 Hz, 3.0 Hz), 5.18 (d, H-1; 3.5 Hz), 5.09 (dd, H-2'; 3.5 Hz, 10.5 Hz), 5.04 (dd, H-4; 9.5 Hz, 10.0 Hz), 4.97 (d, H-1'; 3.5 Hz), 4.76 (dd, H-2; 3.5 Hz, 10.0 Hz), 4.22 (ddd, H-5'; 1.0 Hz, 7.0 Hz, 6.5 Hz), 4.09 (dd, H-6'a; 6.5 Hz, 11.0 Hz); 4.03 (dd, H-6'b; 7.0 Hz, 11.0 Hz), 3.93 (ddd, H-5; 10.0 Hz, 5.0 Hz, 2.5 Hz), 3.70 (dd, H-6a; 5.0 Hz, 11.5 Hz), 3.60 (2 dd, α-H; 9.5 Hz, 6.0 Hz); 3.53 (dd, H-6b; 2.5 Hz, 11.5 Hz), 3.22 (dd, α'-H; 9.5 Hz, 6.0 Hz), 2.12 (s, 3 H, Ac), 2.11 (s, 3 H, Ac), 2.04 (s, 3 H, Ac), 2.03 (s, 6H, 2 Ac), 2.00 (s, 3H, Ac), 1.96 (s, 3H, Ac), 1.57 ($m_c$, β-H), 1.36-1.17 (m, 24H, $CH_2$), 0.87 (2 t, 6H, $CH_3$) ppm.

Example 2

2-Octyl-dodecyl β-maltoside

Yield: 35%; Cr 19° C. SmA 115° C. Cub 192° C. Col 210° C. I $^1$1-1-NMR (400 MHz, $CDCl_3$, peracetate): δ 5.34 (d, H-1'; 4.0 Hz), 5.29 (dd, H-3'; 10.0 Hz, 10.0 Hz), 5:18 (dd, H-3; 9.0 Hz, 9.0 Hz), 4.98 (dd, H-4'; 10.0 Hz, 10.0 Hz), 4.79 (dd, H-2'; 4.0 Hz, 10.0 Hz), 4.75 (dd, H-2; 8.0 Hz, 9.5 Hz), 4.41 (2 d, H-1; 8.0 Hz), 4.39 (dd, H-6a; 3.0 Hz, 12.0 Hz), 4.18 (dd, H-6'a; 4.0 Hz, 12.0 Hz), 4.17 (dd, H-6b; 4.5 Hz, 12.0 Hz), 3.97 (dd, H-6'b; 2.5 Hz, 12.0 Hz), 3.93 (dd, H-4; 9.0 Hz, 9.5 Hz), 3.90 (ddd, H-5'; 10.0 Hz, 4.0 Hz, 2.5 Hz), 3.71 (dd, α-H; 9.5 Hz, 5.5 Hz), 3.59 (ddd, H-5; 9.5 Hz, 3.0 Hz, 4.5 Hz), 3.22 (dd, α-H; 9.5 Hz, 6.5 Hz), 2.07 (s, 3H, Ac), 2.03 (s, 3H, Ac), 1.97 (s, 3H, Ac), 1.95 (s, 3H, Ac), 1.93 (s, 911, 3 Ac), 1.47 (m, β-H), 1.29-1.11 (m, 32H, $CH_2$), 0.81 (2 t, 6H, $CH_3$) ppm.

Example 3

2-Decyl-tetradecyl β-maltoside

Yield: 40%; Cr 19° C. SmA 73° C. Cub 131° C. Col 225° C. I

Example 4

2-Ethyl-hexyl α-maltoside

Yield: 21%; Cr 74 ° C. I $^1$H-NMR (300 MHz, $CDCl_3$, peracetate): δ 5.50 (dd, H-3; 10.0 Hz, 8.5 Hz), 5.38 (d, H-1'; 4.0 Hz), 5.36 (dd, H-3'; 10.5 Hz, 9.5 Hz), 5.04 (dd, H-4'; 9.5 Hz, 10.0 Hz), 4.92 (H-1; 4.0 Hz), 4.85 (dd, H-2'; 4.0 Hz, 10.5 Hz), 4.70 (2 dd, H-2; 4.0 Hz, 10.0 Hz), 4.43 (dd, H-6*; 2 Hz, 12 Hz), 4.23 (dd, H-6*; 4 Hz, 12 Hz), 4.22 (dd, H-6*; 3.5 Hz, 12 Hz), 4.03 (dd, H-6*; 2 Hz, 12 Hz), 4.00-3.89 (m, 3 H, H-4, H-5, H-5'), 3.61/3.60 (2 dd, α-H; 9.5 Hz, 6.5 Hz), 3.24/3.22 (2 dd, α-H'; 9.5 Hz, 6.0 Hz), 2.12 (s, 3H, Ac), 2.08 (s, 3H, Ac), 2.05 (s, 3H, Ac), 2.02 (s, 3H, Ac), 2.01 (s, 3H, Ac), 1.99 (s, 6H, 2 Ac), 1.55 ($m_c$, β-H), 1.44-1.18 (m, 8H, $CH_2$), 0.91-0.84 ($m_c$, 6H, $CH_3$) ppm.

Example 5

2-Hexyl-decyl α-maltoside

Yield: 18%; Cr 123° C. SmA 224° C. Dec

Example 6

2-Hexyl-decyl β-cellobioside

Yield: 38%; Cr? SmA 189° C. dec $^1$H-NMR (400 MHz, $CDCl_3$, peracetate): δ 5.17 (dd, H-3*; 10.0 Hz, 9.5 Hz), 5.12 (dd, H-3*; 10.0 Hz, 9.5 Hz), 5.04 (dd, H-4'; 9.5 Hz, 10.0 Hz), 4.89 (dd, H-2*; 8.0 Hz, 10.0 Hz), 4.87 (dd, H-2*; 8.0 Hz, 10.0 Hz), 4.49 (d, H-1*; 8.0 Hz), 4.48 (dd, H-6a*; 2.0 Hz, 12.0 Hz), 4.39 (d, H-1*; 8.0 Hz), 4.34 (dd, H-6a*; 4.5 Hz, 12.5 Hz), 4.07 (dd, H-6b*; 5.0 Hz, 12.0 Hz), 4.03 (dd, H-6b*; 2.0 Hz, 12.5 Hz), 3.75 (dd, H-4; 10.0 Hz, 10.0 Hz), 3.73 (dd, α-H; 9.5 Hz, 6.0 Hz), 3.64 (ddd, H-5*; 10.0 Hz, 2.0 Hz, 4.5 Hz), 3.55 (ddd, H-5*; 10.0 Hz, 2.0 Hz, 5.0 Hz), 3.25 (dd, α'-H; 9.5 Hz, 6.0 Hz), 2.11 (s, 3H, Ac), 2.08 (s, 3H, Ac), 2.01 (s, 3H, Ac), 2.00 (s, 6H, 2 Ac), 1.99 (s, 3H, Ac), 1.96 (s, 3H, Ac), 1.50 ($m_c$, β-H), 1.30-1.18 (m, 16H, $CH_2$), 0.86 ($m_c$, 6H, $CH_3$) ppm.

Example 7

2-Decyl-tetradecyl β-lactoside

Yield: 26%; Cr 117° C. Col 235° C. I $^1$H-NMR (400 MHz, $CDCl_3$, peracetate): δ 5.31 (bd, H-4'; 3.5 Hz, <1 Hz), 5.16 (dd, H-3; 9.5 Hz, 9.5 Hz), 5.07 (dd, H-2'; 8.0 Hz, 10.5 Hz), 4.91 (dd, H-3'; 10.5 Hz, 3.5 Hz), 4.86 (dd, H-2; 8.0 Hz, 9.5 Hz), 4.44 (d, H-1*; 8.0 Hz), 4.44 ($m_c$, H-6*), 4.38 (d, H-1*; 8.0 Hz), 4.12-4.01 (m, 3H, H-6*), 3.83 (bdd, H-5'; <1 Hz, 7 Hz, 7 Hz), 3.76 (dd, H-4; 9.5 Hz, 9.5 Hz), 3.55 ($m_c$, H-5), 3.72 (dd, α-H; 9.5 Hz, 5.0 Hz), 3.23 (dd, α'-H; 9.5 Hz, 5.0 Hz), 2.12 (Int 3, s, Ac), 2.08 (s, 3H, Ac), 2.03 (s, 3H, Ac), 2.01 (s, 6H, 2 Ac), 1.98 (s, 3H, Ac), 1.93 (s, 3H, Ac), 1.58 ($m_c$, β-H), 1.30-1.16 (m, 40H, $CH_2$), 0.84 (t, 6H, $CH_3$) ppm.

Example 8

2-Decyl-tetradecyl α-lactoside

Yield: 5% (+20% α/β-mixture~5:3)

Cr 93° C. SmA 142° C. Cub 164° C. Col 182° C. I $^1$H-NMR (270 MHz, $CDCl_3$, 3,6,2',3',4',6'-hexaacetate): δ 5.34 (bd, H-4'; 3.0 Hz), 5.19 (dd, H-3; 10.0 Hz, 9.5 Hz), 5.12 (dd, H-2'; 8.0 Hz, 10.5 Hz), 4.95 (dd, H-3'; 10.5 Hz, 3.0 Hz), 4.80 (d, H-1'; 4.0 Hz), 4.49 (d, H-1'; 8.0 Hz), 4.40 (dd, H-6*a; 2.0 Hz, 12.0 Hz), 4.21-4.02 (m, 3H, 3 H-6*), 3.87 (bdd, H-5'; 7 Hz, 7 Hz), 184 ($m_c$, H-5), 3.65 (dd, H-4; 9.5 Hz, 9.5 Hz), 3.62 (dd, α-H; 9.5 Hz, 6.0 Hz), 3.54 (dd, H-2; 10.0 Hz, 4.0 Hz), 3.30 (dd, a'-H; 9.5 Hz, 6.0 Hz), 2.15 (s, 3H, Ac), 2.12 (s, 3H, Ac), 2.11 (s, 3H, Ac), 2.05 (s, 3H, Ac), 2.04 (s, 3H, Ac), 1.96 (s, 3H, Ac), 1.60 (mc, β-H), 1.40-1.15 (m, 40H, $CH_2$), 0.87 (t, 6H, $CH_3$) ppm.

It is to be understood that the present invention may be embodied in other specific fours and is not limited to the sole embodiment described above. However modification and equivalents of the disclosed concepts such as those which readily occur to one skilled in the art are intended to be included within the scope of the claims which are appended thereto.

The invention claimed is:

1. Glycolipids of saturated branched chain alkyl oligosaccharides, the glycolipids having at least one derivative of an amine contained therein, the glycolipids having a structural formula of

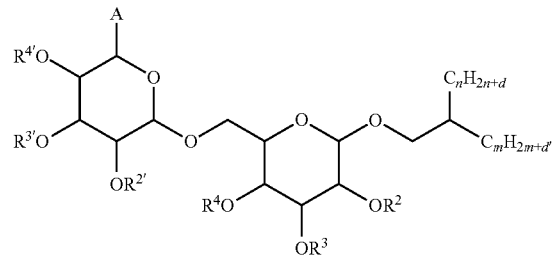

wherein
$A=CH_2Y$, $CH_3$, $CH_2OL$, $C_2H_4W$;
L=H or any sugar;
$R^2$=H;
$R^{2'}$=H
$R^3$=H;
$R^{3'}$=H;
$R^4$=H;
$R^{4'}$=H;
R*=(substituted) alkyl or aryl;
W=OH, NHC(=W*)R*, or NH(=W*)Y*R*;
Y=X, Cl, Br, F, $N_3$ or CN;
W*, Y*=O, S, or NR*;
m and n≥3, m≠n; and
d and d' is 1.

2. Glycolipids of saturated branched chain alkyl oligosaccharides, the glycolipids having at least one ethylene oxide contained therein, the glycolipids having a structural formula of

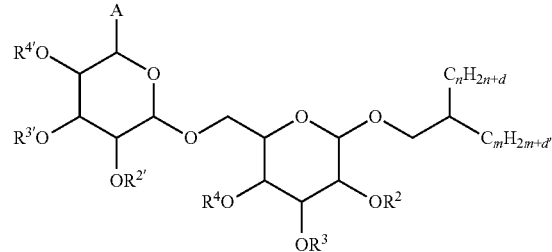

wherein
A=H, $CH_2Y$, $CH_2OL$, $CH_3$, or $CO_2R^*$;
L=H or any sugar;
$R^2$=H or $(C_2H_4O)_xH$;
$R^{2'}$=H or $(C_2H_4O)_xH$;
$R^3$=H or $(C_2H_4O)_xH$;
$R^{3'}$=H or $(C_2H_4O)_xH$;
$R^4$=H or $(C_2H_4O)_xH$;
$R^{4'}$=H or $(C_2H_4O)_xH$;
R*=(substituted) alkyl, aryl, or H;
W=OH, NHAc, or $O(C_2H_4O)_xR^*$;
Y=W, Cl, Br, F, $N_3$ or CN;
X is an integer of 1 to 100;
m and n≥3, m≠n; and
d and d' is 1.

* * * * *